OAK TREE
Filed Oct. 23, 1973 3 Sheets-Sheet 1
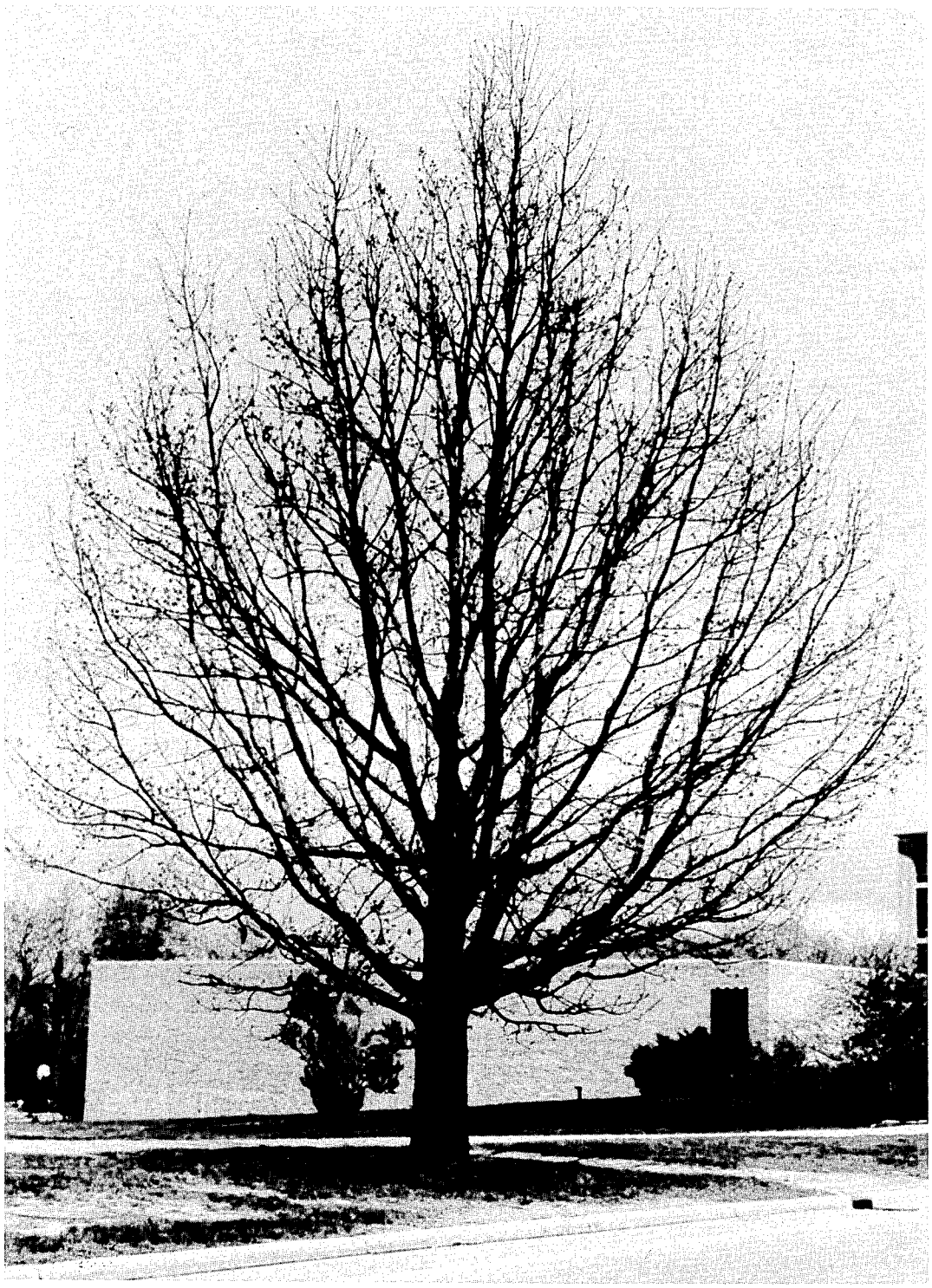

OAK TREE
Filed Oct. 23, 1973 3 Sheets-Sheet 2
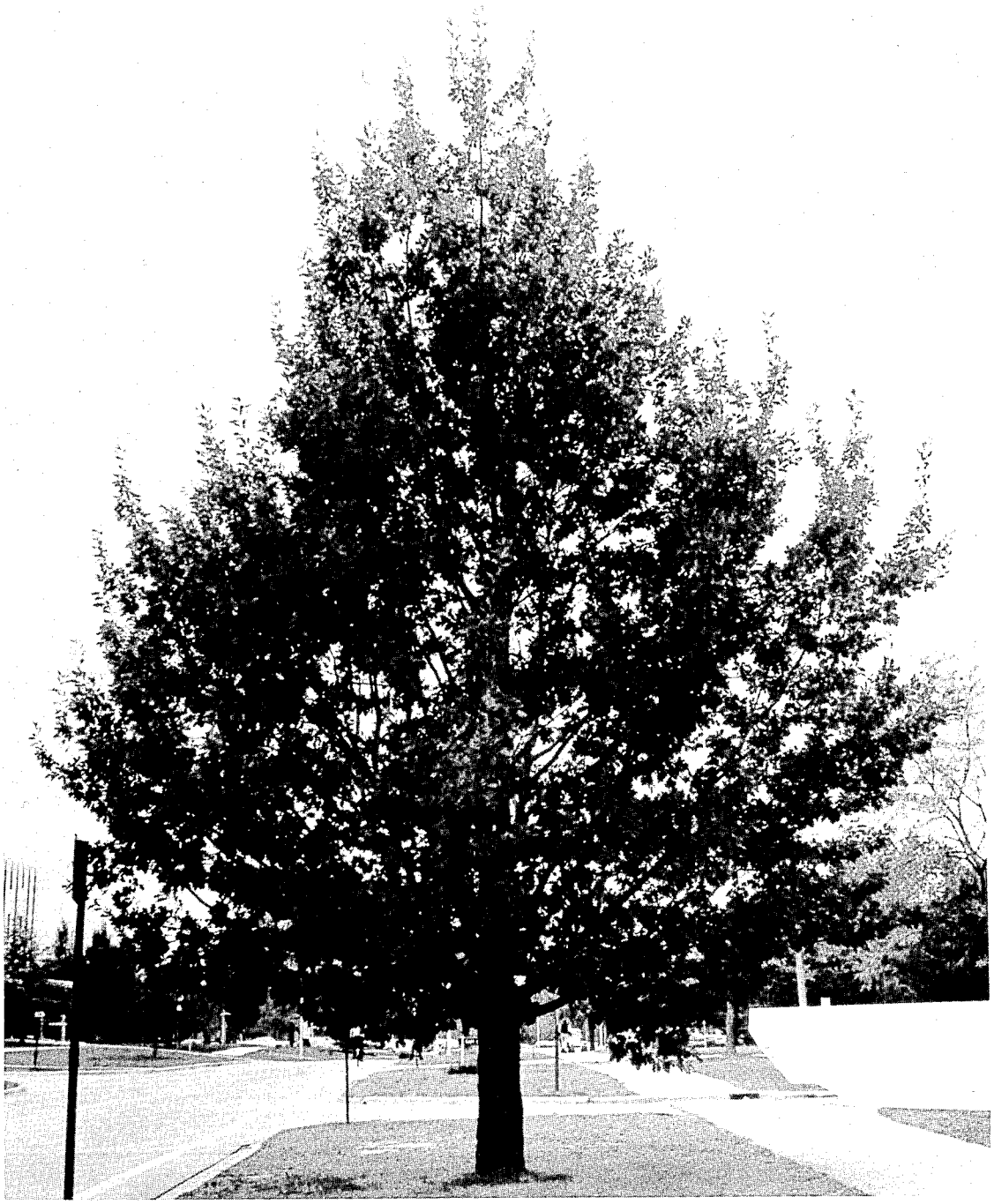

OAK TREE
Filed Oct. 23, 1973 3 Sheets-Sheet 3
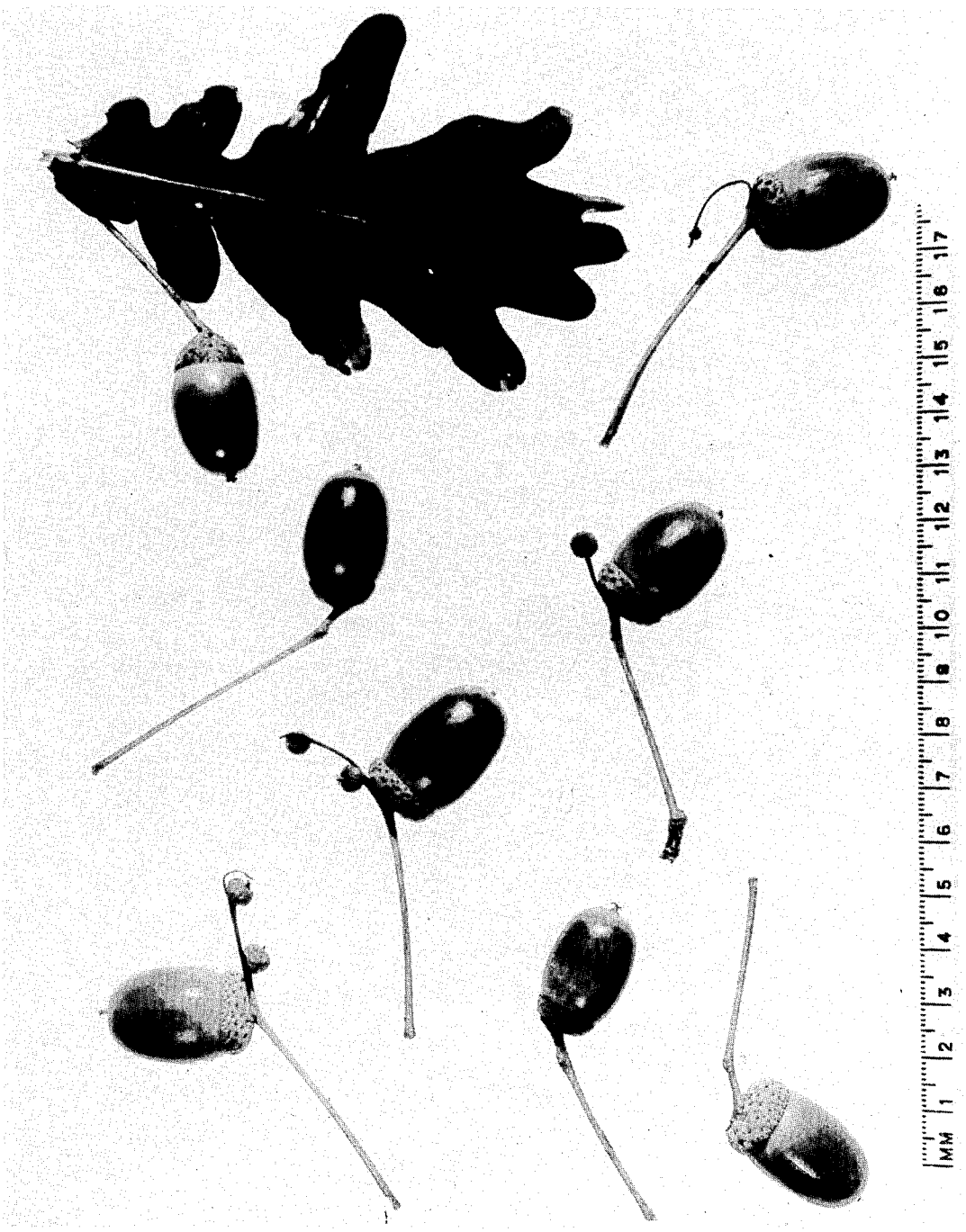

United States Patent

Plant Pat. 3,706

Patented Apr. 22, 1975

3,706

OAK TREE

Milton Baron, Haslett, Mich., assignor to J. Frank Schmidt and Son Co., Troutdale, Oreg.

Filed Oct. 23, 1973, Ser. No. 408,828

Int. Cl. A01h *5/12*

U.S. Cl. Plt.—51 1 Claim

The present invention relates to a new and distinct variety of English oak tree of the species botanically known as *Quercus robur*, which was discovered and developed by me as a selected cultivated seedling of unknown parentage, among a group of plants of this species being grown under my supervision and control at Michigan State University at East Lansing, Mich.

Over many years, the University has collected or received by gift, or otherwise reproduced, many seedling shade trees, and the present new English oak seedling, among hundreds of others (many grown from acorns produced thereby), have been undergoing tests and experimental developments in the University Campus Nursery and on the campus grounds at East Lansing since 1946. When the Dutch Elm Disease (DED) became epidemic in this area starting about 1961, these English oak seedlings were even more closely scrutinized as likely substitutes for American elms. Over this extended period of observations, four salient traits bearing on the overall landscape suitability of the English oak have emerged:

A. Ease of transplanting in late winter or spring;
B. Low maintenance qualities as manifested by
   (a) exceptional ability to withstand severe environmental stress resulting from compacted soil, restricted root run, extended drought, gale winds and ice storms;
   (b) absence of any need over a period of nearly three decades to initiate programs to control insects or disease;
C. Long-persisting foliage casting effective shade until late October (and later farther south); and
D. Pronounced variability in form and growth rate, the latter varying 300% from about 6 inches to over 18 inches annually.

The first three of these traits (A, B, and C) qualify the English oak (including the instant variety) as a prime candidate for urban plantings requiring many individuals of one kind, such as boulevard and street plantings.

The fourth trait (D), in equally decisive fashion precludes the English oak from assuming its rightful place among the finest of trees for urban planting when grown from seeds (acorns). Because of its notorious variability, it simply cannot be recommended for any use where landscape specifications demand uniform crown proportions and growth rate in order to achieve integrated landscape design. Furthermore, this variability is evident even among seedling progeny from a single seed parent, as demonstrated by marked differences in growth rate observed among 9,000 two-year old seedlings grown by me from a single high-producing campus tree in 1964.

Finally, seedlings grown from acorns produced within the range of our native *A. alba* and *Q. Macrocarpa* have the potential for an even wider range of variability as illustrated by several putative hybrids that have also been grown by me on the University campus aforesaid.

Clearly then, the English oak cannot fulfill its great promise in the absence of asexual propagration. Such propagation of a superior selected variety, tailored to perform a specific landscape role, and made economically feasible by patent protection, constitutes a first step in converting the notorious variability of this species from a handicap to a virtue. Vegetative propagation of the subject variety makes available a horticulturally and esthetically ideal candidate for any landscape function calling for a stately tree having a predictable symmetrical ovoid crown with a rugged branching habit.

As the result of my prolonged observations and tests, I am convinced that the selected seedling which is the subject hereof is definitely a new and distinct variety, as particularly evidenced by the following unique combination of primary characteristics which are outstanding therein and which distinguish the same from all other varieties of English oak trees of which I am aware:

(1) A stately tree with a gracefully symmetrical ovoid crown having a height/width ratio of 1.15;
(2) Main scaffold branches arising in the lower third of the crown, with their trend of ascent averaging 37° from the vertical;
(3) The upper two-thirds of the trunk bearing only small branches and, except for position, being scarcely distinguishable from the upper portions of the rugged scaffold branches;
(4) Sturdy, wide-angle crotches of about 65°;
(5) Attractive leathery leaves which are dark green and lustrous above, and pale blue-green below; and
(6) Very scanty fruit production, in some years being none at all.

It may be noted above that several of the primary characteristics by which the subject variety is distinguished from the species deal with the internal structure of the crown. Though of no great significance esthetically, they are of overriding concern from the viewpoint of maintenance and longevity.

Asexual reproduction of my new seedling by soft budding on potted 2-year seedlings, as performed under my direction and supervision at the Beaumont Nursery of Michigan State University, shows that the foregoing characteristics and distinctions come true and are established and transmitted through succeeding propagations.

The accompanying drawings show typical mature tree specimens of my new English oak variety while in foliage as well as bare of foliage, and also a typical specimen leaf and typical specimens of the fruit (acorns).

The following is a detailed description of the new variety, with color terminology in accordance with general color terms of ordinary dictionary significance, since the color features are not materially significant or different from those normal to the species:

A large ovoid tree, with a crown height/width ratio of 1.15 and rugged branches originating low on the trunk and forming the main framework of the crown; crotches diverging from the trunk at an angle of about 65°, with the trend of branch ascent shortly changing to an average of 37°; bark dark, deeply furrowed, forming irregular plates; twigs glabrous, with those of the second year shiny gray-brown, and of the first year greenish brown; buds clearly 5-angled, glabrous except for the sparsely villous margins of the scales, with the lateral divergent; leaves glabrous, with the blade rather leahery, lustrous dark green above and paler below, obvate, mostly 12–15 (11.1–16.0) cm. long and 6–9 (5.3–10.2) cm. broad, pinnately lobed, with 5–7 pairs of rounded lobes separated by obtuse to acute sinuses reaching about half-way to the midrib, base auriculate, falcate ears variously refluexed or inequilateral, frequently clasping the 5–10 mm. petiole; fruits very sparsely produced, usually borne singly on a relatively slender peduncle, 1.2 mm. in diameter and 4–5 (6.5) cm. long, with the acorn being shiny brown, short-ellipsoid, about 2.3 cm. long and 1.6 cm. in diameter; cup thin-walled, shallow bowl-shaped, enclosing about 1/10 of the acorn and being about 5 mm. deep and 1.4 cm. in diameter, with the outer surface smooth except for the scarious free tips of the glabrous scales.

I claim:

1. A new and distinct variety of English oak tree of the species botanically known as *Quercus robur,* substantially as herein shown and described, characterized particularly as to novelty by the unique combination of a stately tree with a gracefully symmetrical ovoid crown having a height/width ratio of 1.15; main scaffold branches arising in the lower third of the crown, with their trend of ascent averaging 37° from the vertical; the upper two-thirds of the trunk bearing only small branches and, except for position, being scarcely distinguishable from the upper portions of the rugged scaffold branches; sturdy, wide-angle crotches of about 65°; attractive leathery leaves which are dark green and lustrous above, and pale blue-green below; and very scanty fruit production, in some years being none at all.

References Cited

New Illustrated Encyclopedia of Gardening, Everett, 1960, Greystone Press, pp. 1748–9 relied on.

ROBERT E. BAGWILL, Primary Examiner